United States Patent
Eungard et al.

(10) Patent No.: US 6,832,715 B2
(45) Date of Patent: Dec. 21, 2004

(54) GUIDEWIRE DISTAL TIP SOLDERING METHOD

(75) Inventors: Todd D. Eungard, Maple Grove, MN (US); Alan C. Matzen, Blaine, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 47 days.

(21) Appl. No.: 10/008,447

(22) Filed: Dec. 3, 2001

(65) Prior Publication Data

US 2003/0102360 A1 Jun. 5, 2003

(51) Int. Cl.[7] .......................... B23K 1/20; B23K 31/02; B23K 31/00; B23K 35/36
(52) U.S. Cl. ..................... 228/207; 228/248.1
(58) Field of Search ................ 228/224, 222, 228/245, 207, 223, 248.1; 29/173; 128/662.06; 604/280; 606/108; 600/585

(56) References Cited

U.S. PATENT DOCUMENTS

| | | |
|---|---|---|
| 4,080,706 A | 3/1978 | Heilman et al. |
| 4,634,042 A * | 1/1987 | Smith ...................... 228/173.4 |
| 4,724,846 A | 2/1988 | Evans, III |
| 4,811,743 A | 3/1989 | Stevens |
| 4,884,579 A | 12/1989 | Engelson |
| 4,925,445 A | 5/1990 | Sakamoto et al. |
| 5,067,489 A | 11/1991 | Lind |
| 5,095,915 A | 3/1992 | Engelson |
| RE33,911 E | 5/1992 | Samson et al. |
| 5,213,111 A | 5/1993 | Cook et al. |
| 5,449,369 A | 9/1995 | Imran |
| 5,458,585 A | 10/1995 | Salmon et al. |
| 5,488,959 A | 2/1996 | Ales |
| 5,497,786 A | 3/1996 | Urick |
| 5,542,434 A | 8/1996 | Imran et al. |
| 5,551,443 A | 9/1996 | Sepetka et al. |
| 5,605,162 A | 2/1997 | Mirzaee et al. |
| 5,606,981 A | 3/1997 | Tartacower et al. |
| 5,664,580 A | 9/1997 | Erickson et al. |
| 5,695,111 A * | 12/1997 | Nanis et al. ................. 228/206 |
| 5,697,380 A * | 12/1997 | Quiachon et al. ........... 600/585 |
| 5,776,079 A * | 7/1998 | Cope et al. .................. 600/585 |
| 5,830,155 A | 11/1998 | Frechette et al. |
| 5,873,835 A * | 2/1999 | Hastings et al. ............. 600/488 |
| 5,916,166 A | 6/1999 | Reiss et al. |
| 5,921,958 A | 7/1999 | Ressemann et al. |
| 6,039,743 A * | 3/2000 | Quiachon et al. ........... 606/108 |
| 6,113,557 A | 9/2000 | Fagan et al. |
| 6,142,958 A | 11/2000 | Hammarström et al. |
| 6,306,105 B1 | 10/2001 | Rooney et al. |

FOREIGN PATENT DOCUMENTS

| | | |
|---|---|---|
| EP | 0 468 645 A1 | 1/1992 |
| WO | WO 99/19018 | 4/1999 |

* cited by examiner

Primary Examiner—Stanley S. Silverman
Assistant Examiner—Colleen P. Cooke
(74) Attorney, Agent, or Firm—Crompton, Seager & Tufte LLC

(57) ABSTRACT

A guidewire manufacturing assembly and method of forming an improved distal tip on a guidewire are disclosed. A guidewire may be an elongate shaft, a coil disposed along the length of the shaft, a holding fixture coupled to the shaft, a solder ball disposed to flux, and a heat source disposed proximate the solder ball to partially melt the solder ball and allow formation of an atraumatic distal tip.

14 Claims, 1 Drawing Sheet

GUIDEWIRE DISTAL TIP SOLDERING METHOD

BACKGROUND OF THE INVENTION

1. Field of the Invention

The present invention pertains to guidewires for use with intravascular catheters. More particularly, the present invention pertains to guidewires with an improved, atraumatic distal tip.

2. Description of the Related Art

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

Intravascular catheters are commonly used in conjunction with a guidewire. A guidewire may be advanced through the patient's vasculature until it has reached a target location. Once in place, a catheter may be threaded onto the guidewire and urged distally until the distal end of the catheter reaches a target location.

The vasculature of a human being can be a very tortuous path. In order for a guidewire to be steered through the vasculature, it may be beneficial for the guidewire to be flexible, particularly near the distal end. Increased flexibility may be incorporated into a guidewire in a number of differing ways. For example, the distal tip of the guidewire may be tapered.

A coil may be disposed about the guidewire, for example to provide support and/or strength. It may be desirable for the coil to be secured to the guidewire. This may be accomplished by welding a portion of the coil to the inner core member of the guidewire. Welding may require the use of a heat sink to help absorb some of the heat generated during welding. Following welding, the heat sink may be removed by grinding. Grinding may also serve to smooth the distal tip.

BRIEF SUMMARY OF THE INVENTION

The present invention pertains to a refinement of guidewires. More particularly, the present invention pertains to guidewires with an improved distal tip. The distal tip may include an atraumatic solder tip. The atraumatic tip may help to secure a coil to the inner shaft of the guidewire. Moreover, the atraumatic tip may be formed by performing a minimal amount of processing steps.

The guidewire may include an inner elongate shaft having a coil disposed along at least a portion of its length. A solder ball may be disposed at the distal end of the shaft and a quantity of flux may be disposed proximate the solder ball. A heat source may be disposed proximate the solder ball for heating the solder ball to a temperature where at least a portion of the solder ball may be melted. Heating the solder ball may activate the flux and result in flow of molten solder proximally. Solder remaining at the distal end of the shaft may form the atraumatic distal tip. A holding fixture may be coupled to the shaft that may comprise a heat sink to draw away or absorb heat. A heat shrink tube may also be coupled to the shaft to stop proximal migration of flux and/or solder.

DETAILED DESCRIPTION OF THE INVENTION

Figure 1:
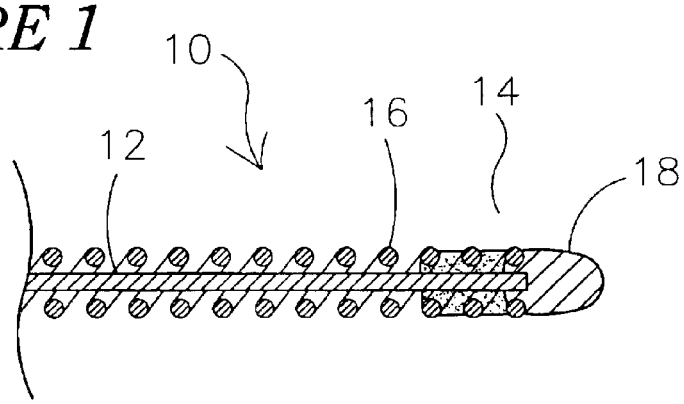
FIG. 1 is a cross-sectional view of a guidewire with an atraumatic distal tip.

The following description should be read with reference to the drawings wherein like reference numerals indicate like elements throughout the several views. The detailed description and drawings illustrate example embodiments of the claimed invention.

FIG. 1 is a cross-sectional view of a guidewire with an atraumatic distal tip. A guidewire 10 comprises an elongate shaft 12 having a distal end 14, a coil 16, and an atraumatic distal tip 18. Atraumatic distal tip 18 is formed by partially melting a solder ball 22 that is dipped in or otherwise coupled to a quantity of flux 24. A portion of the partially molten solder ball 22 may migrate proximally along shaft 12 when heated, leaving behind distal tip 18 at distal end 14. Proximal flow of solder ball 22 may also serve the function of coupling coil 16 to shaft 12.

Tip 18 has a generally smooth texture and rounded shape. Moreover, the shape and texture of tip 18 may result without any additional steps of grinding, filing, or smoothing. The method of forming atraumatic distal tip 18 may also include the use of a heat sink (described below) to draw heat away from guidewire 10. By drawing heat away from guidewire 10, localized heat effected areas that may weaken the strength of guidewire 10 may be minimized.

Shaft 12 may be comprised of materials including, but not limited to, metals, stainless steel, nickel alloys, nickel-titanium alloys, thermoplastics, high performance engineering resins, fluorinated ethylene propylene (FEP), polymer, polyethylene (PE), polypropylene (PP), polyvinylchloride (PVC), polyurethane, polytetrafluoroethylene (PTFE), polyether block amide (PEBA), polyether-ether ketone (PEEK), polyimide, polyamide, polyphenylene sulfide (PPS), polyphenylene oxide (PPO), polysulfone, nylon, perfluoro (propyl vinyl ether) (PFA), and combinations thereof.

Shaft 12 may be distally tapered. According to this embodiment, shaft 12 may further comprise a plurality of distal segments or comprise a single, generally tapered distal end 14. Each distal segment may comprise a decreased outside diameter or individual segments may each taper along the length of a particular segment. A person of ordinary skill in the art could appreciate that a vast number of alternate configurations of segments and distal ends may be included without departing from the scope of the invention.

Coil 16 may be comprised of materials similar to those listed above. For example, coil 16 may be comprised of a stainless steel wire. According to this embodiment, coil 16 may have an outside diameter of about, for example, 0.002 to 0.0030 inches and be disposed about shaft 12 with a pitch of about, for example, 0.0024 to 0.0032 inches per turn.

In addition, a portion of coil 16 may be comprised of radiopaque materials. A radiopaque coil is understood to be capable of producing a relatively bright image on a fluoroscopy screen or another imaging technique during a medical procedure. This relatively bright image aids the user of guidewire 10 in determining the location of distal end 14 of shaft 12. Radiopaque materials may include, but are not limited to, gold, platinum, tungsten alloy, and plastic material loaded with a radiopaque filler. Guidewire 10 may further comprise additional radiopaque markers. It should be understood that coil 16, alternatively, may comprise a plurality of coils. According to this embodiment, an individual segment of coil 16 may be comprised of radiopaque materials.

Figure 2:
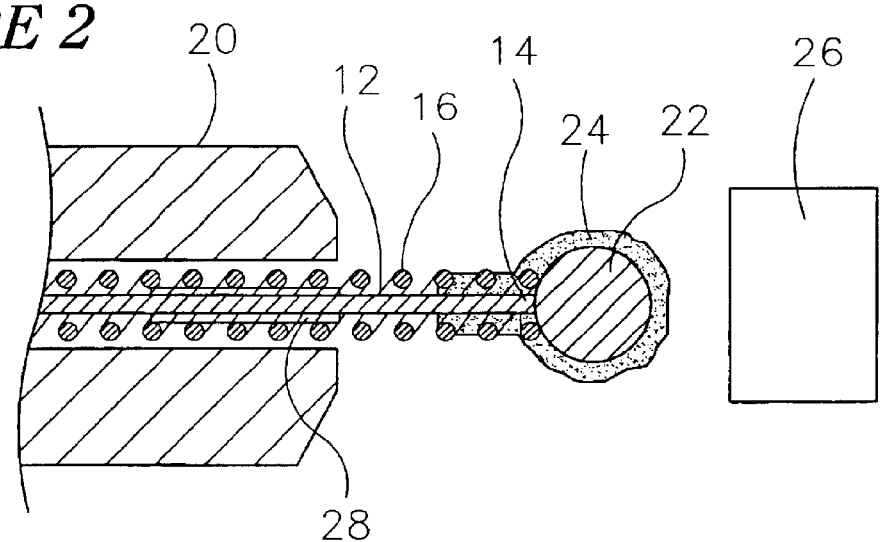
FIG. 2 is a plan view of the guidewire wherein a holding fixture and a heat shrink tube are coupled to the shaft.

FIG. 2 is a plan view of guidewire 10 wherein a holding fixture 20 is coupled to shaft 12. Holding fixture 20 may comprise a heat sink. A heat sink is understood to be a structure that substantially absorbs heat from a given location. Holding fixture 20 may be used to hold guidewire 10 stationary during the formation of atraumatic distal tip 18. Holding fixture 20 may be used with guidewire 10 in a horizontal or a vertical orientation.

Solder ball 22 may be coupled to distal end 14 of elongate shaft 12. Solder ball 22 may be used to form atraumatic tip 18. Solder ball 22 may be radiopaque and useful for imaging guidewire 10. In addition, solder ball 22 may have an outside diameter of about 0.012 to 0.020 inches. Solder ball 22 can be generally spherical in shape. A person of ordinary skill in the art would be familiar with different sizes and shapes of solder ball 22 that may be appropriate for multiple embodiments of the invention.

Solder ball 22 is coupled to a quantity of flux 24. Flux 24 is understood to be a substance applied to parts of a surface or surfaces to be joined, acting on application of heat to prevent oxide formation and facilitate the flowing of solder. Solder ball 22 may be coupled to flux 24, for example, by dipping solder ball 22 into flux 24. Flux 24 may be used to couple solder ball 22 to distal end 14 of elongate shaft 12. Distal end 14 of shaft 12 may be aligned flush with an end of coil 16. According to this embodiment, flux 24 may have a surface tension that may secure solder ball 22 to distal end 14 of elongate shaft 12. Alternatively, flux 24 may include adhesive properties that may assist the coupling of solder ball 22 to shaft 12.

A heat source 26 may be disposed proximate solder ball 22. It should be understood that multiple locations of heat source 26 relative to solder ball 22 may be used without departing from the scope of the invention, for example behind or under solder ball 22. Heat source 26 may be capable of increasing the temperature of solder ball 22 such that at least a portion thereof melts. For example, heat source 26 may have a temperature of about 460° C. Alternatively, heat source 26 may have a temperature up to about, for example, 600° C. or greater. The heat cycle time that solder ball 22 is exposed to heat source 26 may also vary. For example, the cycle time of exposure may be up to about 5 seconds or more.

Heat source 26 may be used to form atraumatic distal tip 18. Heating may activate flux 24 and allows solder ball 22 to at least partially melt and flow into coil 16 and around shaft 12. Atraumatic tip 18 may be formed by solder remaining at distal end 14 of shaft 12 after heating. After heating, little or no flux 24 will remain due to flux 24 being incinerated. In an exemplary embodiment, additional processing of guidewire 10 may not be required such as grinding, filing, smoothing, etc.

When activated, flux 24 migrates proximally along shaft 12. The proximal migration of flux 24 may contribute to the size and shape of atraumatic distal tip 18 since migration of flux 24 may facilitate the flow of solder. For example, if flux 24 migrates a great distance proximally, a greater quantity of molten solder (i.e., from solder ball 22) may flow proximally into coil 16 and about shaft 12. The greater the quantity of solder that is allowed to flow proximally, the smaller the quantity of solder remaining at distal end 14 of shaft 12 for the formation of atraumatic distal tip 18. Moreover, if flux 24 is allowed to migrate too far proximally, it is possible that not enough solder may remain for the formation of atraumatic distal tip 18. Holding fixture 20, therefore, may be positioned along shaft 12 so as to prevent flux 24 from migrating too far proximally and altering the formation of atraumatic distal tip 18.

Guidewire 10 may further comprise a heat shrink tube 28 coupled to shaft 12. Heat shrink tube 28 may be used to prevent proximal migration of flux 24 similar to what is described above and may provide a barrier for the prevention of proximal migration of flux 24. Heat shrink tube 28 may be comprised of polytetrafluoroethylene and coupled to shaft 12. Heat shrink 28 may remain coupled to shaft 12 after manufacturing of guidewire 10 or may be removed after manufacturing.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of forming an atraumatic distal tip on a guidewire, comprising:
   providing an elongate shaft having a distal end and a coil disposed along a length of the shaft;
   providing a solder ball;
   providing a quantity of flux proximate the solder ball;
   disposing the solder ball at the distal end of the shaft; and
   heating the solder ball, wherein heating activates the flux and allows the solder ball to at least partially melt and flow into the coil and around the shaft, wherein an atraumatic tip is formed by solder remaining at the distal end of the shaft.

2. The method in accordance with claim 1, wherein the step of providing a quantity of flux proximate the solder ball includes dipping the solder ball in the flux.

3. The method in accordance with claim 1, wherein the step of providing a quantity of flux proximate the solder ball includes disposing the flux at the coil proximate the distal end of the shaft.

4. The method in accordance with claim 1, further comprising a step of coupling the shaft to a holding fixture, wherein the holding fixture holds the shaft in a vertical orientation.

5. The method in accordance with claim 1, wherein the guidewire further comprises a heat shrink tube coupled to the shaft.

6. The method in accordance with claim 5, wherein the heat shrink tube stops proximal flow of flux during the step of heating the solder ball.

7. A method of forming an atraumatic distal tip on a guidewire, comprising:
   providing an elongate shaft having a distal end a coil disposed along a length of the shaft;
   coupling the shaft to a holding fixture;
   providing a solder ball;
   providing a quantity of flux proximate the solder ball;
   disposing the solder ball at the distal end of the shaft; and
   heating the solder ball, wherein heating activates the flux and allows the solder ball to at least partially melt and flow into the coil and around the shaft, wherein an atraumatic tip is formed by solder remaining at the distal end of the shaft.

8. The method in accordance with claim 7, wherein the step of providing a quantity of flux proximate the solder ball includes dipping the solder ball in the flux.

9. The method in accordance with claim 7, wherein the step of providing a quantity of flux proximate the solder ball includes disposing the flux at the coil proximate the distal end of the shaft.

10. The method in accordance with claim 7, wherein the holding fixture holds the shaft in a horizontal orientation.

11. The method in accordance with claim 7, wherein the holding fixture holds the shaft in a vertical orientation.

12. The method in accordance with claim 7, wherein the guidewire further comprises a heat shrink tube coupled to the shaft.

13. The method in accordance with claim 12, wherein the heat shrink tube stops proximal flow of flux during the step of heating the solder ball.

14. A method of forming an atraumatic distal tip on a guidewire, comprising:

providing an elongate shaft having a distal end and a coil disposed along a length of the shaft;

coupling the shaft to a holding fixture, whereby the holding fixture holds the shaft in a horizontal orientation;

providing a solder ball;

providing a quantity of flux proximate the solder ball;

disposing the solder ball at the distal end of the shaft; and heating the solder ball, wherein heating activates the flux and allows the solder ball to at least partially melt and flow into the coil and around the shaft, wherein an atraumatic tip is formed by solder remaining at the distal end of the shaft.

* * * * *